United States Patent [19]

Harandi et al.

[11] Patent Number: 4,840,928
[45] Date of Patent: Jun. 20, 1989

[54] CONVERSION OF ALKANES TO ALKYLENES IN AN EXTERNAL CATALYST COOLER FOR THE REGENERATOR OF A FCC UNIT

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 144,990

[22] Filed: Jan. 19, 1988

[51] Int. Cl.$^4$ .................. B01J 38/30; C10G 11/18; C07C 5/333

[52] U.S. Cl. .......................... 502/41; 208/78; 208/113; 208/160; 208/164; 585/301; 585/666; 585/910

[58] Field of Search .................. 208/113, 120, 78, 79, 208/46, 49, 69, 70, 164, 160; 502/31, 38, 41; 585/324, 330, 666, 910, 301

[56] References Cited

U.S. PATENT DOCUMENTS

| | | | |
|---|---|---|---|
| 2,397,352 | 3/1946 | Hemminger | 260/683.3 |
| 2,772,217 | 11/1956 | Nicholson | 502/41 |
| 2,784,826 | 3/1957 | Drews et al. | 502/41 |
| 3,392,110 | 7/1968 | Payne | 208/160 |
| 3,894,934 | 7/1975 | Owen et al. | 208/78 |
| 3,907,663 | 9/1975 | Owen | 208/70 |
| 4,152,393 | 5/1979 | Callahan et al. | 422/144 |
| 4,293,722 | 10/1981 | Ward et al. | 585/330 |
| 4,404,090 | 9/1983 | Castillo et al. | 208/52 CT |
| 4,422,925 | 12/1983 | William et al. | 208/75 |
| 4,551,229 | 11/1985 | Pecoraro et al. | 208/76 |
| 4,578,366 | 3/1986 | Centinkaya et al. | 502/6 |
| 4,614,726 | 9/1986 | Walters et al. | 502/41 |
| 4,640,763 | 2/1987 | Chou | 208/78 |
| 4,675,461 | 6/1987 | Owen et al. | 585/330 |

Primary Examiner—Anthony McFarlane
Attorney, Agent, or Firm—Alexander J. McKillop; Charles J. Speciale; L. G. Wise

[57] ABSTRACT

Lower alkanes are converted to olefins in a 'third bed' external catalyst cooler (ECC) in which hot catalyst, from the regenerator ('second bed') operating in conjunction with a fluid catalytic cracker ('first bed'), thermally cracks and dehydrogenates the alkanes. Because this is an endothermic reaction, the catalyst is autogeneously cooled before it is recirculated to the FCC regenerator. The cracking catalyst is the catalyst of choice in the FCC reactor. The most evident benefit of using the ECC is that it eliminates internal regenerator coils for steam regeneration. Among several additional benefits is that the ECC allows flexibility in design of its fluid 'third bed' for optimum weight hourly space velocity (WHSV), and control of the dehydrogenation temperature so as to get maximum conversion of alkanes. This conversion can be maintained because the FCC regenerator burns the coke made during alkane dehydrogenation. The ECC also permits control of the temperature at which the FCC regenerator operates so as to facilitate processing heavier than conventionally used feedstock in the FCC unit resulting in better earnings.

12 Claims, 2 Drawing Sheets

CONVERSION OF ALKANES TO ALKYLENES IN AN EXTERNAL CATALYST COOLER FOR THE REGENERATOR OF A FCC UNIT

BACKGROUND OF THE INVENTION

Catalyst from a fluid catalyst cracking (FCC) unit is regenerated because it is contaminated with coke ("coked up") in an operating fluid bed catalytic cracker. An FCC regenerator operates at very high temperatures due to the high heat release of burning coke. The capacity of many FCC units is limited by the regenerator operating at a temperature which approaches the limit beyond which the regenerator may not be operable because of its metallurgy. Hot regenerated catalyst (regen catalyst) is conventionally cooled in a catalyst cooler ("catcooler") by generating steam. The catcooler may be either internal or external. In this invention we cool the regen catalyst in an external catalyst cooler (ECC) which also functions as a dehydrogenation reactor to which alkanes are fed.

More specifically, this invention relates to coupling the dehydrogenation of a lower $C_2$-$C_6$ alkane, preferably propane ($C_{3p}$) and butane ($C_{4b}$), and most preferably propane, with the operation of a FCC cracker and its regenerator, in the specific instance where the temperature of operation of the regenerator permits using the FCC catalyst as an effective propane dehydrogenation agent.

As will hereinafter be described and substantiated, the dehydrogenation reaction occurs in the ECC due to thermal catalytic cracking which is partly a pyrolytic thermal reaction, referred to herein as thermal dehydrogenation, and partly a dehydrogenation catalytic effect of the FCC catalyst. Since it is the FCC catalyst which is responsible for the dehydrogenation, we refer to it as "dehydrogenation catalyst" or "ECC catalyst" when it is in the ECC, just as we refer to the catalyst being regenerated as "regen catalyst", though it is only being regenerated. The thermal dehydrogenation of normally liquid hydrocarbons at a temperature in the range from 538° C. to 750° C. (1000-1382° F.) by pyrolysis in the presence of steam, is disclosed in U.S. Pat. Nos. 3,835,029 and 4,172,816, inter alia, but there is no suggestion that such a reaction may be used as the basis for direct heat exchange, to cool regen catalyst in an ECC for a FCC unit.

At the present time, there exists a profusion of schemes for dehydrogenating propane, eventually, for the most part, converting it to gasoline or other products far more valuable than propane. For example, U.S Pat. No. 4,293,722 to Ward et al, teaches one such process. These schemes are unequivocally based on the catalytic effect of particular catalysts and rely on reactions which occur at substantially lower temperatures than those used in our process.

Still more specifically, this invention relates to an improvement in cooling regen catalyst, which improvement involves operating a fluid bed of a conventional FCC catalyst in an ECC under conditions such that the catalyst is cooled while it performs its alkane dehydrogenating function, and having done so, may be returned from the ECC to the regenerator. Conditions of operation of the bed of catalyst in the ECC (ECC bed) is closely tied to the amount of coke deposited during operation of the bed (cracker bed) of FCC catalyst in the cracker, which in turn dictates the amount of heat which will be generated in the bed (regen bed) of catalyst being regenerated in the regenerator. The particular conditions of operation of each of the three fluid beds will be decreed by the mass and energy balances required to accomplish what we have discovered may be done to improve the economics of operation of the FCC section of an oil refinery.

The FCC process converts petroleum feedstocks in the gas oil boiling range to lighter products such as gasoline. Though a wide variety of catalysts may be used in the cracker, most preferred is a zeolite cracking catalyst with a proclivity to be deactivated when coked up. This requires that much coke be removed from the catalyst when it is to be regenerated. As a result, regenerators are designed to be "hot-operated" and under pressure, that is, operated at a pressure in the range from about 25 psig to 40 psig, and as high a temperature as is practical from a materials standpoint. The temperature within a regenerator typically ranges from about 538° C. to about 815° C. (1000°-1500° F.) and the ECC operates in our process, in the same general range of pressure and temperature.

As stated, heat generated in a conventional regenerator is typically removed by internal coils (regen coils) functioning as an internal catcooler, or, by an ECC (external catcooler) in which hot catalyst is contacted with cooling fluid in heat exchanger tubes. Prolonged operation of a regenerator at a temperature at which the catalyst's efficiency is not deleteriously affected bestows upon the operation of any catcooler, a criticality which demands near-absolute reliability of operation. Because such reliability has been so well established by tubes carrying cooling fluid, a heat exchanger is a logical choice, and has been for many years. Because of the relatively high temperature, in the range from about 621° C. to about 732° C. (1150°-1350° F.), at which a large volume of regenerated catalyst must be returned to the cracker of an operating refinery, it will be evident that the drop in catalyst temperature due to cooling it, cannot be large, but the amount of heat to be removed is very large. This makes the generation of steam a logical choice. Since steam generation by indirect heat exchange with boiler feed water carried in tubes, is such a 'perfect fit', the practical onus of cooling regen catalyst by direct heat exchange which is necessarily inflexibly tied to the operation of an unrelated dehydrogenation reaction carried out in yet another (third) fluid bed, if ever given even cursory consideration, must understandably have been viewed with a lack of enthusiasm.

Since the dehydrogenation reaction is endothermic, by providing a fluid bed ECC we have provided a catalyst cooling chamber for removing enough heat from the system to compensate for the large amount generated by the regeneration of the catalyst.

Prior art FCC regenerators with catcoolers are disclosed in U.S. Pat. Nos. 2,377,935; 2,386,491; 2,662,050; 2,492,948; and 4,374,750 inter alia. All these prior art catcoolers remove heat by indirect heat exchange, typically a shell and tube exchanger. None removes heat by direct heat exchange, for example, by continuously diluting hot regenerated catalyst with cold catalyst, or by blowing cold air through the hot catalyst; more particularly, none removes heat by functioning as a reactor which supplies heat to an endothermic reaction.

U.S. Pat. No. 4,422,925 discloses the step-wise introduction of ethane, propane, butane, recycle naphtha, naphtha feed, raffinate naphtha, and fractionator bottoms recycle in the riser reactors of a FCC unit. In the riser reactors, the lower alkanes are contacted, in a transport zone, with hot regenerated catalyst which would dehydrogenate the alkanes, progressively decreasing the temperature of the suspension of catalyst and hydrocarbons as they progress upwards through the risers. The mixture of catalyst and reaction products is then contacted with a hydrocarbon feedstock suitable for catalytic cracking, such as virgin naphtha, virgin gas oil, light cycle gas oil, or heavy gas oil. (see col 2, lines 29–33). Clearly, the control of the catalyst temperature in the risers as well as the benefits of dehydrogenation occurring in the risers were both lost when the products from the risers were mixed with the products of the main cracker. Most important is that operation of the reference FCC unit as a combination dehydrogenator and cat cracker failed to provide control of the olefins generated, which control is essential if recovery and subsequent utilization of the olefins is a goal of the process.

The concept of cooling hot regenerated catalyst by using an endothermic reaction, specifically the catalytic dehydrogenation of butane, was disclosed more than four decades ago in U.S. Pat. No. 2,397,352 to C. E. Hemminger. Though unrelated to operation of a FCC unit, regeneration of the catalyst was required before it was returned to the dehydrogenation reactor. He provided a catalyst (chromic oxide supported on alumina or magnesia) heating chamber for supplying heat to the dehydrogenation reaction to compensate for that lost in the dehydrogenation reaction, and to preheat, at least in part, the butane to raise its temperature to reaction temperatures.

Since the disclosure of this old process, the use of large pore zeolites for cracking catalysts was discovered, as was the effectiveness of certain large and intermediate pore zeolites for the conversion of alkanes to olefins. Our process achieves at least 50%, and preferably 70% conversion of propane, and for the first time, makes the process practical in a refinery environment.

Though conceptually feasible, the '352 system required pressurizing catalyst powder which was to be recirculated. The result was that the catalyst did not recirculate, and over the years, improving upon the concept had been neglected. Particularly because the generation of steam is generally desirable in a typical refinery, and this could be done both reliably and economically with a conventional indirect heat exchanger, the teaching of the '352 was never related to cooling FCC catalyst. The application of the concept of cooling FCC catalyst in an ECC was more fortuitous than by design. It happened that the temperature for dehydrogenation of lower alkanes matched the temperature at which a large pore zeolite cracker catalyst is to be returned to the regenerator. Moreover, we found that the recirculation problem evaporated when the alkane was prevaporized and mixed with the catalyst to be recirculated before the catalyst was introduced into the dehydrogenation chamber.

Though other dehydrogenation processes are available, we have found that the "third bed" catalytic dehydrogenation of propane, tied to the operation of a FCC cracker and regenerator, provides numerous advantages. In addition to the desirable upgrading of ethane ($C_{2p}$), propane ($C_{3p}$) and butane to ethylene ($C_2=$), propylene ($C_3=$) and butylenes ($C_4=$), no prior art process teaches the steps of our process which: (1) affords such flexibility in the design of the ECC 'third bed' for optimum weight hourly space velocity (WHSV), and control of the dehydrogenation temperature so as to get maximum conversion; (2) affords flexibility in controlling the temperature at which the FCC regenerator operates so as to facilitate processing heavier than conventionally used feedstock in the FCC; (3) does not increase the throughput to the FCC reactor and main column system; (4) uses the FCC regenerator to burn coke made during alkane dehydrogenation; (5) eliminates internal regen coils for steam regeneration; and, (6) eliminates the ECC air compressor used to provide fluidization air to a conventional ECC catcooler, because hot propane gas provides the fluidization; and (7) minimizes undesirable thermal cracking in the FCC reactor by reducing the temperature of catalyst fed to the FCC reactor, as more fully described in a particular embodiment in which spent catalyst from the ECC is directly fed to the FCC reactor.

SUMMARY OF THE INVENTION

It has been discovered that alkanes, preferably lower alkanes may be converted to olefins in a 'third bed' ECC in which hot catalyst from an FCC regenerator thermally cracks and dehydrogenates the alkanes, and because this is an endothermic reaction, the catalyst is autogeneously cooled before it is recirculated to the FCC regenerator.

It is therefore a general object of this invention to provide a process for profitably using heat generated in a regenerator of a FCC cracker, comprising utilizing a conventional FCC catalyst which also is an effective thermal dehydrogenating agent for alkanes at a temperature (in an ECC) above that at which the catalyst is to be returned to the regenerator, by transporting hot catalyst from the regeneration zone of the regenerator to a 'third bed' ECC; contacting the hot regen catalyst maintained in a sub-transport zone of a fluid bed in the ECC, with an alkane at a pressure of at least 20 psig (239 kPa), preferably 20–45 psig (239–411 kPa), and a temperature lower than that in the regenerator but above 1000° F. (538° C.), preferably 1100°–1450° F. (593°–788°C.), said ECC being located externally of the cracker and regenerator; withdrawing olefins generated in the ECC in a stream separate from the effluent from the FCC; and, recirculating cooled catalyst preferably having less than 10% by weight of entrained hydrocarbon vapors (based on the total stream recirculated to the cracker) to the regenerator, or to the riser of the FCC reactor, at a temperature below the average operating temperature of the regenerator.

It is a specific object of this invention to feed a substantially paraffinic stream consisting essentially of a major proportion of propane and a minor proportion (relative to the propane) of propylene and ethylene, to an ECC in which a fluid bed of zeolite regen catalyst, promoted with oxides of metals to enhance the dehydrogenation activity of the catalyst, for example oxides of nickel and vanadium, operates at a temperature in the range from about 1200°–1350° F. (649°–732° C.), and pressure in the range from 25 psig to 40 psig (273 to 3777 kPa), whereby a per pass conversion of at least 50%, and preferably more than 70% of the propane is obtained, and the catalyst is concurrently autogenously cooled.

It is another specific object of this invention to feed a predominantly lower alkane feed to the ECC operating as specified hereinabove with a promoted zeolite regen catalyst, and diverting a portion of cooled catalyst being returned directly to the regenerator, so that it may be flow-controlled into the lower portion of a riser of the fluid cracker, preferably near the bottom.

It is also a specific object of this invention to feed a predominantly lower alkane feed to the ECC operating, in addition to its functions set forth hereinabove, as a FCC reactor stripper, because a controlled stream of spent catalyst is withdrawn from the FCC reactor and introduced directly into the ECC. Upon being stripped by the feed and cooled by the endothermicity of thermal dehydrogenation, the catalyst is flow-controlled into a riser of the FCC reactor, near the bottom. For efficient stripping, a minor amount (relative to the feed) of steam is injected into the bottom of the ECC, so that the combined steam and feed is sufficient to strip the hydrocarbons remaining in the spent catalyst efficiently.

BRIEF DESCRIPTION OF THE DRAWING

The foregoing and other objects and advantages of our invention will appear more fully from the following description, made in connection with the accompanying drawings of preferred embodiments of the invention, wherein like reference characters refer to the same or similar parts throughout the views and in which.

DETAILED DESCRIPTION OF PREFERRED EMBODIMENTS

Figure 1:
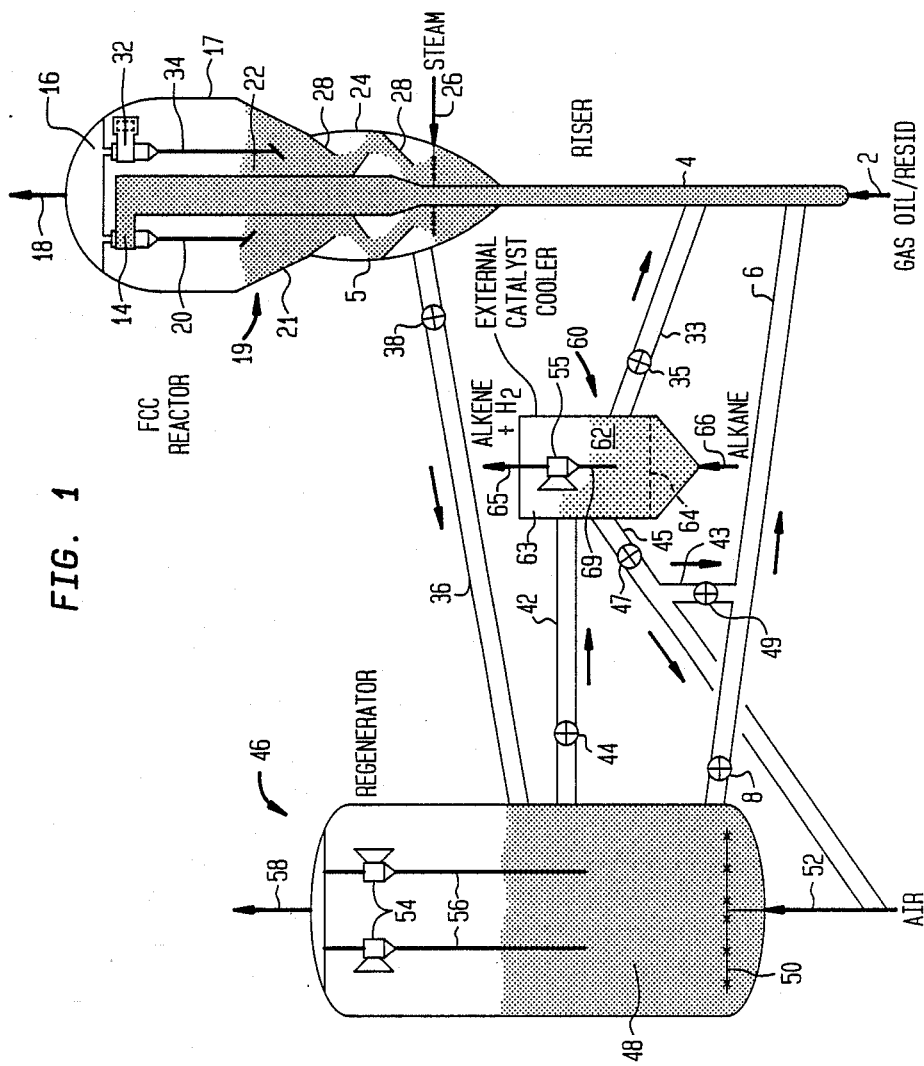
FIG. 1 schematically illustrates a fluidized catalytic cracking unit in which the operation of a regenerator is coupled with that of a fluid bed thermal catalytic cracker and alkane dehydrogenation reactor which also functions as an external catalyst cooler (ECC). This ECC being an endothermic reactor, provides a similar cooling function as that provided by a conventional shell-and-tube heat exchanger used as an ECC.

In a preferred embodiment, the process of this invention is carried out with a cracker catalyst consisting essentially of large pore crystalline silicate zeolite, generally in a suitable matrix component. The particular cracker catalyst used is not critical to initiate the dehydrogenation reaction since part of the reaction is due to thermal cracking. The product yield and selectivity, however, is affected by the catalyst type and its metal content. Most preferred is a rare earth promoted FCC catalyst in which additional metal promoters, particularly nickel and vanadium, are laid down by the vacuum gas oil (VGO) or resid feed to the FCC riser, and the metals are oxidized in the regenerator. In addition, the FCC catalyst may contain a small amount of Pt, usually less than 300 ppm, to boost the oxidation of CO to $CO_2$ in the regenerator. Since control of the distribution of products from the FCC is much more important than control of the distribution of products obtained by dehydrogenation, the preferred catalyst for our process is the FCC catalyst of choice.

Conventional non-zeolitic FCC catalysts may be used which are generally amorphous silica-alumina and crystalline silica-alumina. Other non-zeolitic materials said to be useful as FCC catalysts are the crystalline silicoaluminophosphates of U.S. Pat. No. 4,440,871 and the crystalline metal aluminophosphates of U.S. Pat. No. 4,567,029. However, the most widely used FCC catalysts are large pore crystalline silicate zeolites known to possess some catalytic activity with particular respect to converting lower alkanes to alkenes, and specifically propane to propylene, at a temperature and pressure lower than those at which the regenerator of the FCC unit operates. Such zeolites typically possess an average (major) pore dimension of about 7.0 angstroms and above. Representative crystalline silcate zeolite cracking catalysts of this type include zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), merely to name a few as well as naturally occurring zeolites, such as chabazite, faujasite, mordenite, and the like. Also useful are the silicon-substituted zeolites described in U.S. Pat. No. 4,503,023. Zeolite Beta is yet another large pore crystalline silicate which can constitute a component of the mixed catlayst system herein.

Most preferred is a large pore crystalline silicate zeolite promoted with a catalytic amount of metal or metal oxide of an element selected from Groups V and VIII of the Periodic Table, sufficient to enhance the dehydrogenation activity of the FCC catalyst.

Though typically only one of the aforementioned catalysts is used in a cracker, combinations of two or more may also be used. In addition to the foregoing catalysts, a mixed catalyst system in which a catalyst requiring frequent regeneration, such as zeolite Y, may be employed in combination with a shape selective medium pore crystalline silicate zeolite catalyst requiring comparatively infrequent regeneration such as ZSM-5, as disclosed in copending U.S. patent applications Ser. Nos. 903,311 filed Sept. 3, 1986 by Owen et al, and 060,541 by Avidan et al, filed Nov. 6, 1987, the disclosures of which are incorporated by reference thereto as if fully set forth herein.

The term "catalyst" as used herein shall be understood to apply not only to a catalytically active material but to one which is composited with a suitable matrix component which may or may not itself be catalytically active. By "cracker or cracking catalyst" we refer to any catalyst used in a fluid cracker which catalyst has some propane-dehydrogenation activity under the pressure and temperature conditions specified for operation of the ECC.

The FCC unit is preferably operated under fluidized flow conditions, at a temperature in the range from about 1000° F. to about 1350° F., with a catalyst to charge stock ratio of from about 4:1 to about 20:1, and a contact time of from about 1 to about 20 sec. Generally, it is preferred to crack the charge stock in an upflowing riser conversion zone discharging into cyclonic separation means in an upper portion of an enlarged vessel in which the products of cracking are separated from catalyst.

Preferred charge stocks to the cracker comprise petroleum fractions having an initial boiling point of at least 500° F. (260° C.), a 50% point at least 750° F. (399° C.), and an end point of at least 1100° F. (593° C.). Such fractions include gas oils, thermal oils, residual oils, cycle stocks, whole top crudes, tar sand oils, shale oils, synthetic fuels, heavy hydrocarbon fractions derived from the destructive dehydrogenation of coal, tar, pitches, asphalts, hydrotreated feedstocks derived from anyu of the foregoing, and the like. As will be recognized, the distillation of higher boiling point fractions, above about 750° F. (399° C.) must be carried out under vacuum to avoid thermal cracking. The boiling temperatures utilized herein are expressed, for convenience, in terms of the boiling point corrected to atmospheric pressure.

The separated catalyst is collected in the lower portion of the vessel which is in open communication with the upper end of a lower extending stripping zone wherein the catalyst is stripped with countercurrent upwardly flowing stripping gas, such as steam. The stripped products and products of conversion separate from the catalyst and are discharged from the riser conversion zone. They are combined with the cyclonically separated hydrocarbon vapors and passed to one or more downstream zones. The stripped catlayst is transferred to a regenerator for removal of deposited carbonaceous material by burning, thereby heating the catalyst to a temperature in the range from about 1200° F. 650° C.) to about 1500° F. (815.5° C.).

The foregoing steps in the operation of a FCC unit are conventional, being recited hereinabove only to point out that the conditions at which the steps are practiced, are dictated by the charge stock and the product mix desired, which in turn dictates the operation of the regenerator.

Referring now to FIG. 1, there is schematically illustrated a flowsheet in which a charge stock (feed) 2, such as gas oil (boiling range 600°–1200° F., or 315.5°–676.7° C.) is introduced, after it is preheated, into riser 4, near the bottom. Thus the gas oil is mixed with hot regen catalyst, such as zeolite Y, introduced through a valved conduit means such as standpipe 6 provided with a flow control valve 8. Because the temperature of the hot regenerated catalyst is in the range from about 1200° F. (676.7° C.) to about 1350° F. (732.2° C.), a suspension of hydrocarbon vapors is quickly formed, and flows upward through the riser 4.

The riser 4 is flared gently outward into a region 5 through which catalyst and entrained hydrocarbons are flowed, being afforded, in this region 5, the contact time preselected to provide desired cracked products. Catalyst particles and the gasiform products of conversion continue past region 5 and are discharged from the top of the riser into one or more cyclone separators 14 housed in the upper portion 17 of the vessel, indicated generally by reference numeral 19. Riser 4 terminates in a 'bird cage' discharge device, or an open end "T" connection may be fastened to the riser discharge which is not typically directly connected to the cyclonic catalyst separation means. The effluent from riser 4 comprises catalyst particles and hydrocarbon vapors which are led into the cyclonic separators 14 which effect separation of catalyst from hydrocarbon vapors. Such vapors pass into a plenum chamber 16 and thence are removed through conduit 18 for recovery and further processing.

Hydrocarbon vapors from cyclone 14 are discharged to a plenum chamber 16 from which they flow through conduit 18 for further processing and recovery, typically to a fractionator column where the products of cracking are separated into preselected fractions.

Catalyst separated from the vapors descends through dipleg 20 to a fluid bed 22 of catalyst maintained in the lower portion 21 of the vessel 19. The bed 22 lies above, and in open communication with a stripping zone 24 into which the catalyst progresses, generally downward, and countercurrent to upflowing steam introduced through conduit 26. Baffles 28 are provided in the stripping zone to improve stripping efficiency.

Spent catalyst, separated from the hydrocarbon vapors in the cyclones, is maintained in the stripping zone 24 for a period of time sufficient to effect a higher temperature desorption of feed-deposited compounds which are then carried overhead by the steam. The stripping zone is maintained at a temperature of about 1250° F. or even higher if hot regenerated catalyst is introduced into the stripping zone by means not shown, as is sometimes done. The steam and desorbed hydrocarbons pass through one or more cyclones 32 which return catalyst fines through dipleg 34 to the bed 22.

Stripped catalyst flows though conduit 36, provided with flow control valve 38, to regenerator 46 containing a dense fluid bed 48 of catalyst into the lower portion of which bed, regeneration gas, typically air, is introduced by distributor 50 supplied by conduit 52. Cyclone separators 54 provided with diplegs 56 separate entrained catalyst particles from flue gas and return the separated catalyst to the fluid bed 48. Flue gases pass from the cyclones into a plenum chamber and are removed therefrom by conduit 58. Hot regenerated catalyst is returned to the bottom of riser 4 by conduit 6, to continue the process with another conversion cycle, all of which is conventionally practiced.

In the improvement which is our invention, hot regen catalyst flows though conduit 42, provided with flow control valve 44, to ECC 60 containing a fluid bed 62 of ECC catalyst. As schematically illustrated, the ECC is coupled to the regenerator through the catalyst transfer lines but is physically located externally relative to both the regenerator and the cracker. Into the lower portion of the ECC bed is introduced a feedstream of lower alkanes to be dehydrogenated. Most preferred is a feedstream in which propane is the major constituent relative to the total weight of other hydrocarbon components. The propane is supplied by distributor 64 fed through conduit 66, typically in conjunction with minor amounts of other lower alkanes and even smaller amounts of olefins scavenged from various waste refinery streams. The hot stream of regen catalyst withdrawn from the regenerator is quickly cooled by direct contact with the relatively cool gases and catalyst in the ECC bed.

The ECC generally operates at relatively low WHSV in the range from 0.01 to 5.0 hr$^{-1}$, preferably from 0.1 to 1.0 hr$^{-1}$, and in a relatively narrow pressure and temperature range from above 20 psig to about 50 psig (239–446 kPa), preferably 25 psig to about 45 psig (273–411 kPa), and from about 1200° to 1500° F. (649°–815.5° C.), preferably 1350° F. (732° C.), respectively, depending upon the pressure and temperature at which the regenerator is operated.

The amount of heat supplied to the ECC is determined by a controlled amount of catalyst withdrawn from the regenerator. The rate at which the catalyst stream is withdrawn depends upon the temperature at which the regenerator is to be operated, which in turn determines the amount of alkanes which may be dehydrogenated. For a given flow of regenerated catalyst to the ECC at a preselected temperature, and a given rate of lower alkane charged, the temperature of catalyst in the ECC is controlled in the range from about 1100° to 1350° F. (593°–732° C.) by the temperature to which the charge is preheated.

Cyclone separators 55 provided with a dipleg 69 separates entrained catalyst particles from ethylene, propylene, hydrogen, butylenes, other hydrocarbon products, and unconverted alkanes, and return the separated catalyst to the fluid bed 62. The products of conversion of the dehydrogenation reaction pass from the cyclones into a plenum chamber 63 and are removed therefrom by effluent line 65. Relatively cool ECC catalyst is returned to the regenerator 46 through conduit 45 provided with a valve 47, by being lifted with air in the air-lift conduit 52. If desired, the regenerator may be partly or completely bypassed by flowing the cooled catalyst from the ECC through conduit 33, provided with valve 35, to the riser 4. For greater flexibility of operation, a portion of the cooled catalyst from the ECC is returned to the regenerator through line 45, and the remainder flowed through line 33 to the riser.

Regenerated catalyst is removed from the regenerator through return conduit 6 controlled by valve 8, for passage to the riser 4 of the cracker, either above or below the point where line 33 communicates with the riser. This by-passing of the regenerator by directly flowing cooled catalyst to the FCC riser is desirable in cases where maximizing catalyst circulation and minimizing thermal cracking because of the relatively low catalyst temperature in the FCC riser, is desired.

Again, for additional flexibility of operation, cooled catalyst from the line 45 may be flowed through conduit 43, controlled by valve 49, into the return conduit 6.

Figure 2:
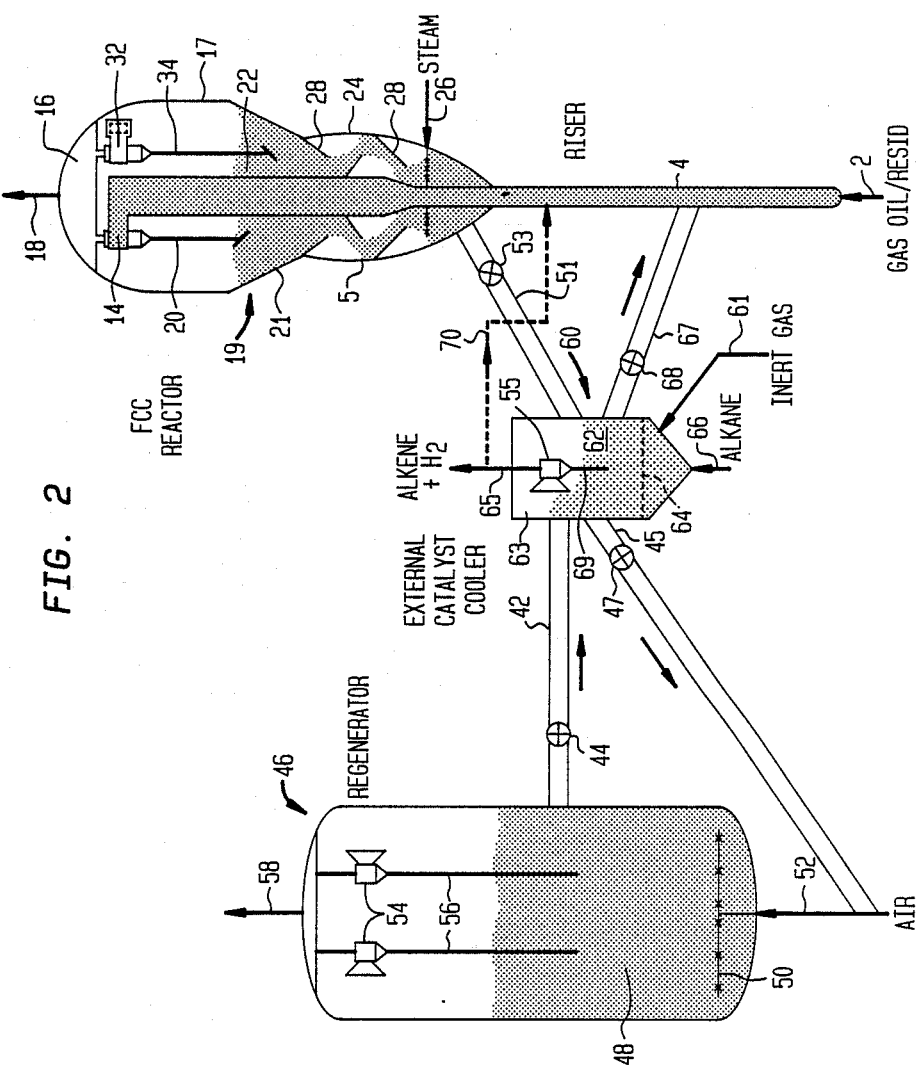
FIG. 2 schematically illustrates the operation of a regenerator from which regen catalyst is cooled in an ECC to which coked up catalyst is flowed from the cracker. A portion of cooled catalyst is flowed from the ECC to a riser of the FCC.

Referring now to FIG. 2 there is schematically illustrated yet another embodiment of the invention which is particularly adapted for the operation of the FCC with resid, but may equally be used for cracking gas oil. In this embodiment, spent catalyst from dip legs 20 and 34 of the FCC, is flowed at from about 1000°–1050° F. (537.8°–565.5° C.) through conduit 51, controlled by valve 53, directly to the ECC 60 so that the alkane feed to the ECC strips hydrocarbons remaining in the pores of the catalyst. The ECC preferably operates at a pressure in the range from 25–45 psig (273–411 kPa) and a temperature in the range from about 1200°–1400° F. (649°–760° C.).

To aid in the stripping, an inert gas stream unreactive with the hydrocarbons under the operating conditions of the ECC, typically steam, optionally in combination with a portion of the alkane feed to be dehydrogenated, may be injected through line 61 into the ECC in an amount sufficient to effect the stripping. A slipstream 70 of effluent from the effluent line 65 may be introduced into the riser 4, if desired. The superficial velocity of alkane in the ECC is preferably in the range from about 0.3 to 5 ft/sec, and that of the steam from 0 to 0.2 ft/sec. It will be found that a lower superficial velocity than 0.3 ft/sec of alkane is not generally economical, and neither is more than 0.2 ft/sec of steam. Cooled catalyst from the ECC is returned through conduit 67, controlled by valve 68, directly to the FCC riser 4. Thus, it will now be evident that the ECC replaces the conventional function of a stripper for the FCC cracker.

The preferred conditions of operation of the ECC are such that about 70% of the propane fed is converted per pass at a WHSV which is no greater than 1 hr$^{-1}$. Higher conversions are obtained with butanes, and lower conversions with ethane.

As may be expected in a thermal dehydrogenation reaction, the conversion and selectivity depends mainly upon the specific process conditions of operation of the ECC, and only to a minor extent upon the particular FCC catalyst being used, unless the catalyst is promoted with specific promoters which enhance the dehydrogenation activity of the FCC catalyst. Most preferred promoters for a faujasite catalyst are nickel and vanadium oxides. Since FCC catalyst captures nickel and vanadium in the FCC feed, dehydrogenation activity of the FCC catalyst is enhanced after it is regenerated. In all instances, the selectivity of conversion from propane to propylene decreases as the conversion increases at a preselected temperature. Also, propane conversion increases as the reaction temperature increases or space velocity decreases. The extent of side reactions such as propane cracking, oligomerization of propylene and ethylene, dehydrogenation of ethane, and isomerization of $C_4$s may be reduced at higher space velocity, but at the expense of propane conversion. In most instances, even when conversion is relatively high, unconverted propane is preferably recycled to the ECC.

The following illustrative example describes a FCC unit processing 2000 barrels/hour of gas oil/resid feed in conjunction with a single stage regenerator. The dense bed of the regenerator has an inventory of 150 short tons (136.07 metric tons) of catalyst.

A faujasite FCC catalyst promoted with nickel is used which is to be regenerated at a temperature no higher than 1500° F. (815° C.) to prevent damage to the catalyst. The catalyst is to be conveyed to the riser of the cracker at a temperature of 1250° F. (746° C.).

Accordingly, 10 tons/minute of hot regen catalyst is withdrawn and mixed into the ECC 60 while 1000 lb/min (453.6 kg/min) of a lower alkane feedstream which is preheated to a temperature of 500° F. (260° C.) by heat exchange (not shown) with products from the overhead effluent of the cracker, are used to maintain the ECC catalyst in a fluidized regime. The particular level of turbulence is not critical so long as the zone is sub-transport, but it is preferred that the regime be sufficiently turbulent that the fluidization is adequate to effect the heat transfer to cool the hot regen catalyst. The lower alkane feedstream is premixed with the hot regen catalyst so as to function as lift-gas lifting the catalyst into the regenerator.

Thus, it will now be evident that the ECC provides a means for adding cooling capacity to an existing regenerator while upgrading a lower alkane stream. The addition of an ECC allows one to feed heavier feedstock to the FCC which will deposit more carbon on the FCC catalyst. The additional heat released by burning off the carbon is compensated for in the ECC while alkanes are converted to more valuable olefins. The valving to vary the flow of catalyst to the ECC, and control the flow from the ECC to the regenerator, permits positive control over operation of the regenerator while it operates "as hot as practical". The process conditions in the ECC make it feasible to control the conversion of at least one alkane in the feedstream so that the effluent from the ECC which comprises alkanes, olefins and hydrogen including minor amounts of aromatics and cycloaliphatics, may be used as feedstock to be upgraded in other sections of the refinery.

The regenerator dimensions and temperature are as follows:

Height 90 ft. (27.43 meters) Diameter 25 ft. (7.62 meters)
Hot catalyst removed from regenerator 21,000 lb/min (9,525.6 kg/min), and flowed to ECC
Temperature of hot regen catalyst 1350° F. (732° C.)

The dimensions of the ECC and conditions of operation with the faujasite catalyst, are as follows:

Height: 60 ft. Diameter: 10 ft. (3.048 m)
Height of fluidized bed: 30 ft. (9.144 m)
Density of fluidized bed: 31 lb/ft$^3$ (496.56 kg/m$^3$)
Average temperature of ECC bed: 1250° F. (676.7° C.)

Superficial velocity of alkane in ECC: 1.2 ft/sec (0.365 m/sec)

WHSV: 0.8 hr$^{-1}$

Temperature of cooled ECC catalyst recycled to regenerator: 1250° F. (676.7° C.)

Having thus provided a general discussion, and a specific illustration of the present invention, and described the dehydrogenation of an alkane feedstream in support thereof, it is to be understood that no undue restrictions are to be imposed by reason thereof except as provided by the following claims.

We claim:

1. In a process for regenerating a coke-contaminated fluid cracking catalyst in a regeneration zone at a pressure in the range from above 20 psig to about 50 psig and a temperature in the range from about 1200° F. to about 1500° F. (650° C. to 815° C.) while injecting enough oxygen-containing regeneration gas into said regeneration zone to maintain a dense fluid bed of regeneration catalyst, and regenerate the catalyst before returning it to a fluid cracker, the improvement comprising, (a) withdrawing a controlled stream of said regenerator catalyst and introducing it into a dehydrogenation zone at a temperature below those prevailing in said regeneration zone, said dehydrogenation zone being located in a catalyst cooler, externally relative to said cracker and regenerator, the amount of said stream being sufficient to supply the endothermic heat of reaction for dehydrogenation of alkanes in said dehydrogenation zone, (b) introducing a feedstream of said alkanes into said dehydrogenation zone in an amount sufficient to maintain hot withdrawn catalyst in a state of fluidization in said catalyst cooler, said state of fluidization existing in a sub-transport regime operating at a weight hourly space velocity WHSV of said lower alkanes not to exceed 5 hr$^{-1}$ while maintained at a temperature high enough to convert at least 50% of said alkanes, and concurrently to cool said catalyst, (c) transporting cooled catalyst directly from said dehydrogenation zone, said catalyst now at a temperature in the range from about 1100°–1350° F. (649°–731° C.), to said regeneration zone, and mixing hot catalyst therein with said cooled catalyst, and, (d) withdrawing products of dehydrogenation in an effluent stream from said catalyst cooler.

2. The process of claim 1 wherein said alkanes are lower alkanes having from 2 to about 6 carbon atoms.

3. The process of claim 2 further comprising, transporting said cooled catalyst for flow-controlled introduction into a riser of said fluid cracker, in the lower portion thereof.

4. The process of claim 2 further comprising, diverting a portion of said cooled catalyst being transported to said regeneration zone, and flow-controlled introducing said portion into a riser of said fluid cracker, in the lower portion thereof.

5. The process of claim 2 wherein said feedstream includes a major amount by weight of propane in relation to the total weight of other hydrocarbons.

6. The process of claim 2 wherein said cracking catalyst is a zeolite catalyst optionally promoted with a catalytic amount of a metal or metal oxide of an element from Group V or VIII sufficient to enhance the dehydrogenation activity of said zeolitic catalyst.

7. The process of claim 2 wherein said effluent stream from said catalyst cooler contains a controlled quantity of at least one olefin.

8. The process of claim 2 further comprising, withdrawing a controlled stream of spent catalyst from said fluid cracker and introducing said spent catalyst directly into said dehydrogenation zone, and transporting said cooled catalyst for flow-controlled introduction into a riser of said fluid cracker, in the lower portion thereof.

9. The process of claim 8 further comprising, introducing a minor amount relative to said alkanes, of steam into said dehydrogenation zone, said amount being sufficient, in combination with said alkanes to strip hydrocarbons remaining in said spent catalyst.

10. The process of claim 8 wherein said feedstream includes a major amount by weight of propane in relation to the total weight of other hydrocarbons.

11. The process of claim 8 wherein said cracking catalyst is a zeolite catalyst optionally promoted with a catalytic amount of a metal or metal oxide of an element from Group V or VIII sufficient to enhance the dehydrogenation activity of said zeolitic catalyst.

12. The process of claim 8 wherein said effluent stream from said catalyst cooler contains a controlled quantity of at least one olefin.

* * * * *